United States Patent [19]

Ishige et al.

[11] Patent Number: 4,842,979
[45] Date of Patent: Jun. 27, 1989

[54] BLACK COLOR HEAT-SENSITIVE DIAZO MICROCAPSULE RECORDING MATERIAL WITH BENZOYLACETIC AMIDE COUPLER

[75] Inventors: Sadao Ishige, Kanagawa; Toshimasa Usami, Shizuoka; Hiroshi Kamikawa, Shizuoka; Toshiharu Tanaka, Schizuoka, all of Japan

[73] Assignee: Fuji Photo Film Co., Ltd., Kanagawa, Japan

[21] Appl. No.: 129,350

[22] Filed: Nov. 30, 1987

Related U.S. Application Data

[63] Continuation of Ser. No. 813,206, Dec. 24, 1985, abandoned.

[30] Foreign Application Priority Data

Dec. 27, 1984 [JP] Japan .................... 59-278859

[51] Int. Cl.$^4$ .................... G03C 1/58; B41M 5/18
[52] U.S. Cl. .................... 430/138; 430/148; 430/151; 430/173; 430/179; 430/182; 430/388; 503/214; 503/218
[58] Field of Search .......... 430/138, 151, 182, 179, 430/173, 388, 148; 503/214, 218

[56] References Cited

U.S. PATENT DOCUMENTS

| | | | |
|---|---|---|---|
| 2,217,189 | 10/1940 | Süs | 430/182 |
| 2,407,210 | 9/1946 | Weissberger et al. | 430/388 |
| 2,537,919 | 1/1951 | Slifkin | 430/182 |
| 3,056,674 | 10/1962 | Hoffstadt et al. | 430/388 |
| 3,056,675 | 10/1962 | Hoffstadt et al. | 430/388 |
| 3,510,306 | 5/1970 | Yoshida et al. | 430/388 |
| 3,615,575 | 7/1968 | Rauhut | 430/173 |
| 3,725,072 | 4/1973 | Yoshida et al. | 430/388 |
| 4,486,527 | 12/1984 | Kurisu et al. | 430/151 |
| 4,529,681 | 7/1985 | Usami et al. | 430/179 |
| 4,559,297 | 12/1985 | Seto et al. | 430/551 |
| 4,598,035 | 7/1986 | Usami et al. | 430/179 |

FOREIGN PATENT DOCUMENTS 937510  9/1963  United Kingdom ................ 430/173

Primary Examiner—Charles L. Bowers, Jr.
Attorney, Agent, or Firm—Sughrue, Mion, Zinn, Macpeak & Seas

[57] ABSTRACT

A heat-sensitive recording material comprising a support having provided thereon a heat-sensitive layer containing microcapsules containing at least one diazonium salt capable of azo-coupling with 2-hydroxy-3-naphthoic acid anilide to develop a blue color, a 2-hydroxy-3-naphthoic acid amide derivative, a benzoylacetic amide derivative represented by the following formula and a basic substance:

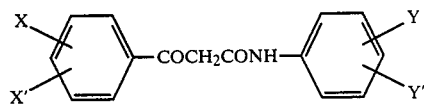

wherein X represents a hydrogen atom, a halogen atom, a lower alkyl group or an alkoxy, aralkyloxy, phenoxy or acylamino group having up to 18 carbon atoms; Y represents an alkyl or aralkyl group having from 7 to 18 carbon atoms, an alkoxy, aralkyloxy, phenoxy, naphthyloxy, alkylthio, aralkylthio or phenylthio group having from 6 to 18 carbon atoms, a naphthylthio group, a sulfonyloxy group, a sulfamoyl gorup, a ureido group, a thioureido group or an acylamino group; X' and Y' each represents a hydrogen atom, a halogen atom, a lower alkyl group or a lower alkoxy group; and Y and Y' may combine to form a substituted or unsubstituted benzene ring. The material has excellent preservability before heat recording, provides a high color density upon heat recording, and develops a black color fixable with light.

8 Claims, No Drawings

BLACK COLOR HEAT-SENSITIVE DIAZO MICROCAPSULE RECORDING MATERIAL WITH BENZOYLACETIC AMIDE COUPLER

This is a continuation of application Ser. No. 06/813,206 filed Dec. 24, 1985, abandoned.

FIELD OF THE INVENTION

This invention relates to a diazo type heat-sensitive recording material which develops a fixable black color and, more particularly, to a heat-sensitive recording material which has excellent preservability before heat recording, provides a high color density upon heat recording, and develops a black color fixable with light after heat recording.

BACKGROUND OF THE INVENTION

In a heat-sensitive recording process, leuco type heat-sensitive recording materials have generally been employed. However, these heat-sensitive recording materials have the disadvantage that color development occurs in unexpected areas due to severe handling or heating after recording or adhesion of solvents and the like, resulting in stains of recorded images. Extensive studies have recently been conducted on diazo type heat-sensitive recording materials free from the above-described disadvantage.

For example, Japanese Patent Application (OPI) No. 123086/82 (the term "OPI" as used herein refers to a "published unexamined Japanese patent application"), *Gazo Denshi Gakkai-Shi*, 11, 290 (1982), disclose diazo type heat-sensitive recording materials containing a diazo compound (diazonium salt), a coupling component and a basic component (inclusive of substances capable of becoming basic upon heating) which are heat-recorded and then irradiated with light to decompose the unreacted diazo compound to thereby stop color formation. According to this process, color formation in unnecessary areas can be effectively prevented; that is, the developed color can be fixed. Nevertheless, these recording materials still exhibit, in some cases, unfavorable coloration (fog) through the gradual progress of pre-coupling during preservation. Therefore, it has been proposed to avoid contact of color forming components by incorporating any one of the color forming components in the form of discontinuous particles, i.e., as a solid dispersion, to thereby prevent pre-coupling. However, preservability of such recording materials before recording (hereinafter referred to as working preservability) is still unsatisfactory and, moreover, there arises the additional disadvantage of reduction in heat developability.

Another proposal to minimize contact between the diazo compound and the coupling component comprises providing these components in independent layers as disclosed, e.g., in Japanese Patent Application (OPI) No. 123086/82. Although this process succeeds in achieving satisfactory improvement of working preservability, the recording materials are impractical due to excessive reduction of heat developability for use in high speed recording having a short pulse width.

In order to satisfy both of working preservability and heat developability, it is also known to separate the coupling component and the basic substance by encapsulizing either one of the two components using non-polar waxy substances (as disclosed in Japanese Patent Application (OPI) Nos. 44141/82 and 142636/82) or hydrophobic high polymers (as disclosed in Japanese Patent Application (OPI) No. 192944/82). In these methods, since the formation of capsules is carried out by dissolving or dispersing the color forming component in a solution of the wax or high polymer in a solvent therefor, the capsules obtained are different from common capsules comprising a core and a shell. When the color forming component is dissolved in the wax or high polymer solution, it is uniformly mixed with the encapsulizing material without forming a core. As a result, pre-coupling gradually proceeds on the interface of capsule walls during preservation so that working preservability cannot be ensured. On the other hand, when the color forming component is dispersed for encapsulization, the color formation reaction does not take place unless the capsule wall is heat-melted, so that heat developability is decreased. Also, the solvent used for dissolving the wax or high polymer should be removed after the formation of capsules.

In order to overcome these problems, the inventors previously developed a process for producing microcapsules comprising a core material containing at least one of the reactants for color formation and capsule walls formed by polymerization to provide excellent heat-sensitive recording materials as disclosed in Japanese Patent Application (OPI) No. 190886/84 (corresponding to U.S. Patent Application Ser. No. 600,267 now abandoned).

However, when the above-described encapsulization process is applied to diazo type heat-sensitive recording materials in which a black color is formed by reacting an appropriate combination of a diazo compound and a coupler, reduction of preservability is sometimes noted and also it is not always easy to stably develop a black color. In particular, a considerable difficulty is encountered in securing stable black color against variation of printing energy of a heat-sensitive printer.

SUMMARY OF THE INVENTION

Accordingly, an object of this invention is to provide a heat-sensitive recording material having excellent preservability and providing a black color with high heat developability.

Another object of this invention is to provide a heat-sensitive recording material which can be fixed by photodecomposition of the unreacted diazo compound after heat recording.

A further object of this invention is to provide a heat-sensitive recording material which is simply and economically produced.

A still further object of this invention is to provide a heat-sensitive recording material which develops a stable hue that does not deviate from black against variation of printing energy.

As a result of extensive and intensive investigations, it has now been found that these and other objects of this invention can be accomplished by a heat-sensitive recording material comprising a support having provided thereon a heat-sensitive layer containing (a) microcapsules containing at least one diazonium salt capable of azo-coupling with 2-hydroxy-3-naphthoic acid anilide to develop a blue color, (b) a 2-hydroxy-3-naphthoic acid amide derivative, (c) a benzoylacetic amide derivative represented by the following formula (I) and (d) a basic substance:

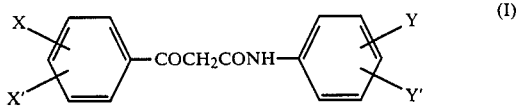

(I)

wherein X represents a hydrogen atom, a halogen atom, a lower alkyl group or an alkoxy, aralkyloxy, phenoxy or acylamino group having up to 18 carbon atoms; Y represents an alkyl or aralkyl group having from 7 to 18 carbon atoms, an alkoxy, aralkyloxy, phenoxy, naphthyloxy, alkylthio, aralkylthio or phenylthio group having from 6 to 18 carbon atoms, a naphthylthio group, a sulfonyloxy group, a sulfamoyl group, a ureido group, a thioureido group or an acylamino group; X' and Y' each represents a hydrogen atom, a halogen atom, a lower alkyl group or a lower alkoxy group; and Y and Y' may combine to form a substituted or unsubstituted benzene ring. It is preferred as the combination of these X, Y, X' and Y' that the total carbon atoms thereof are 6 to 18.

DETAILED DESCRIPTION OF THE INVENTION

The microcapsules according to the present invention are not capsules employed in conventional recording materials which destroyed upon application of heat or pressure whereby a reactant contained in microcapsules and a reactant outside the microcapsules are contacted to cause color formation reaction. Instead, in the microcapsules according to the present invention reactants present inside and/or outside the microcapsules are made permeable through the capsule walls upon the application of heat.

The microcapsules according to the present invention contain at least one diazonium salt capable of azo-coupling with 2-hydroxy-3-naphthoic acid anilide to form a blue color. Outside the microcapsules are present a benzoylacetic amide derivative capable of forming a yellow color, a 2-hydroxy-3-naphthoic acid amide derivative capable of forming a blue color as coupling components, a basic substance, and each in the form of a solid dispersion having a particle size of about 10 μm or less.

The benzoylacetic amide derivative represented by the above-descried formula (I) can be synthesized by condensation of a benzoylacetic ester and an aniline derivative or naphthylamine derivative. Synthesis examples of the benzoylacetic amide derivatives (I) are shown below.

SYNTHESIS EXAMPLE 1

A mixture of 19.2 g of ethyl benzoylacetate, 26.3 g of 4-(4-toluenesulfonyl)hydroxyaniline and 50 ml of xylene was heated at an external temperature of 160° C. to 170° C. for about 2 hours while stirring. The produced ethanol was removed by distillation. After allowing the mixture to cool to room temperature, 50 ml of methanol was added thereto for crystallization. There was obtained 32.5 g of benzoylacetic acid-4'-(4-toluenesulfonyloxy)anilide having a melting point of 198° C. to 200° C.

SYNTHESIS EXAMPLE 2

A mixture of 38.4 g of ethyl benzoylacetate, 12.2 g of 2,4-diaminotoluene and 50 ml of xylene was heated at an external temperature of 165 to 175° C. for about 3 hours while stirring. The produced ethanol was removed by distillation. The residue was allowed to cool to room temperature. To the resulting solid was added 100 ml of methanol, and the mixture was heated under stirring and allowed to cool to room temperature. Filtration gave 33 g of 1,2-bis(benzoylacetamido)benzene having a melting point of 202 to 204° C.

SYNTHESIS EXAMPLE 3

2-(2-Nitrophenyl)thioaniline (72.3 g), which was obtained by reacting 50 g of 1-amino-2-thiophenol and 63 g of 2-nitrochlorobenzene in 160 ml of dimethylformamide in the presence of 56 ml of triethylamine as a dehydrochlorinating agent at room temperature to 50° C. for about 1 hour, and 60.8 g of 2-hydroxy-3-naphthoyl chloride were condensed in a known manner to obtain 90.5 g of 2-hydroxy-3-naphthoic acid-2'-(2-nitrophenylthio)anilide. The product was converted to 67 g of 2-hydroxy-3-naphthoic acid-2'-(2-aminophenylthio)anilide by a hydrazine reduction method, which was then condensed with 211 g of ethyl benzoylacetate in the same manner as in the foregoing synthesis examples to yield 70 g of benzoylacetic acid-2'-[2-(2-hydroxy-3-naphthoylamino)phenylthio]anilide having a melting point of 156° to 158° C.

Specific examples of the benzoylacetic amide derivatives which can be used in the present invention are given below for illustrative purposes only, and are not to be construed as limiting the present invention in any way.

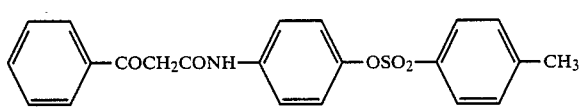

(1)

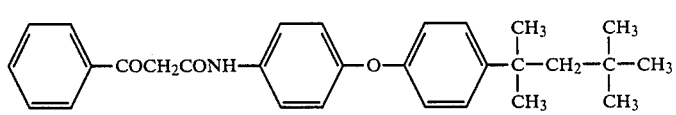

(2)

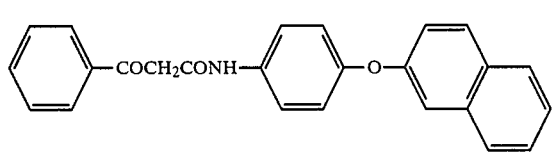

(3)

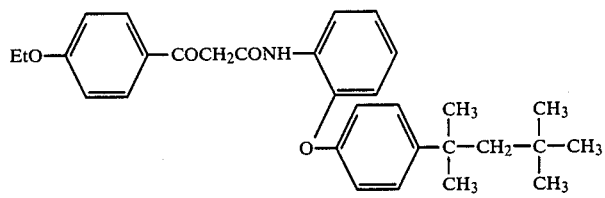 (4)
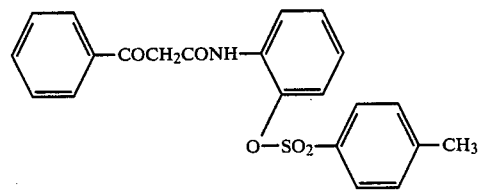 (5)
 (6)
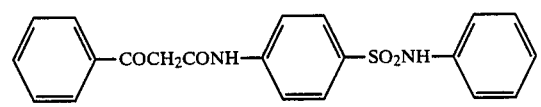 (7)
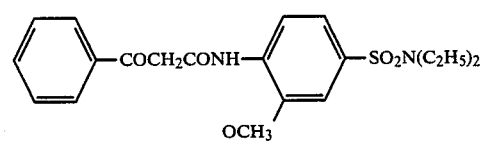 (8)
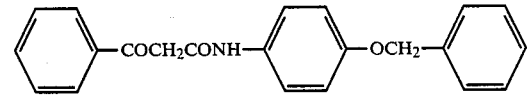 (9)
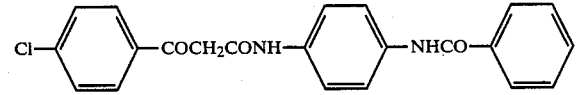 (10)
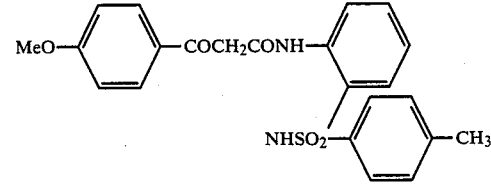 (11)
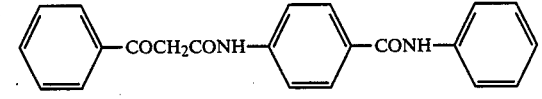 (12)
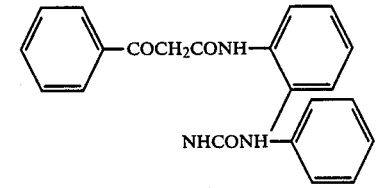 (13)

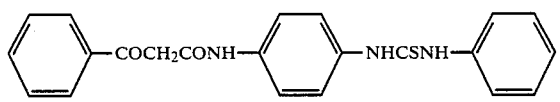 (14)
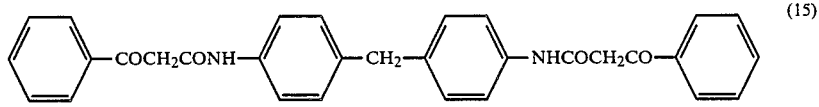 (15)
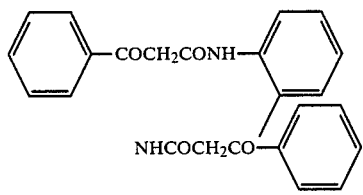 (16)
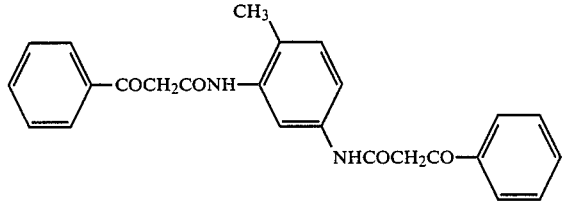 (17)
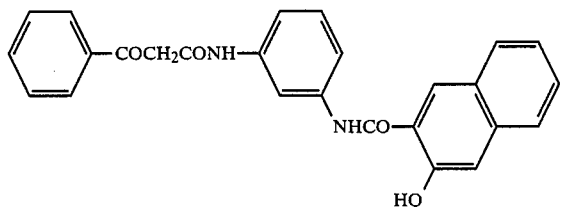 (18)
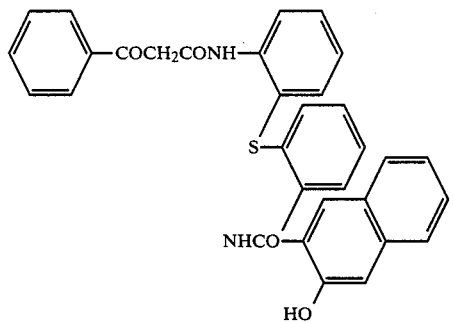 (19)
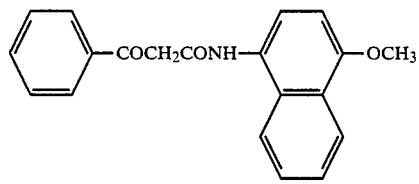 (20)
Specific examples of the 2-hydroxy-3-naphthoic acid amide derivatives which can be used in the present invention are shown below for illustrative purposes only and are not to be construed as limiting the present invention in any way. The 2-hydroxy-3-naphthoic acid amide derivatives having carbon atoms of 17 to 29 are preferred.
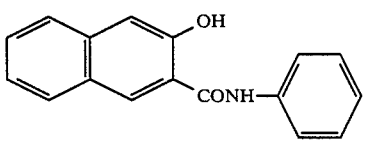 (1)

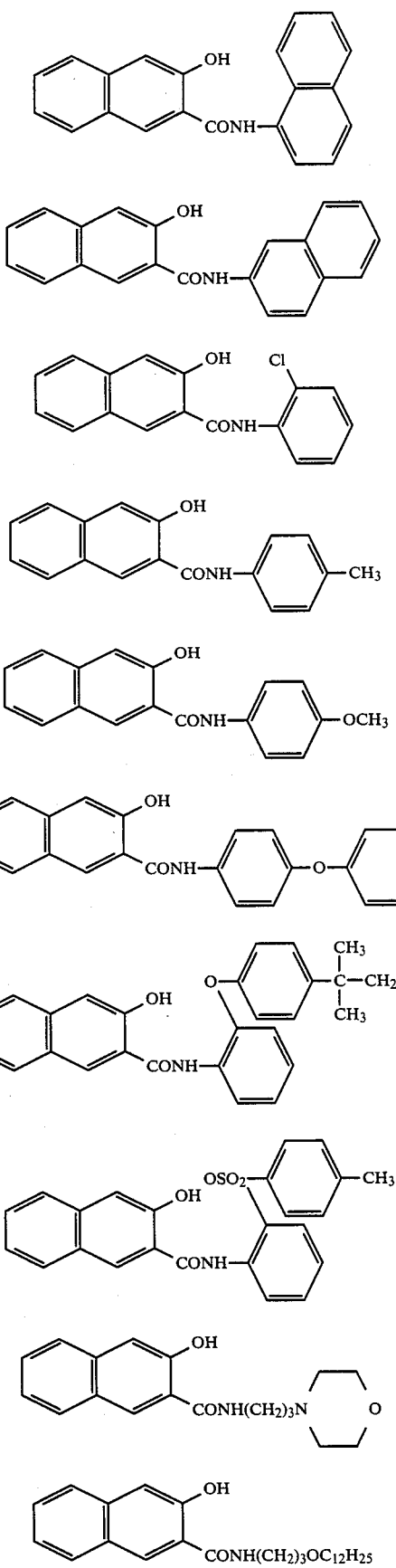

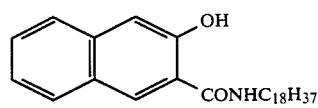

Specific examples of the diazonium salts capable of forming a blue color upon azo-coupling with 2-hydroxy-3-naphthoic acid anilide are shown below for illustrative purposes only, and are not to be construed as limiting the present invention in any way. The sparingly water-soluble diazonium salts having carbon atoms of 16 to 30 are preferred.

The above-described coupling components are preferably used in a total amount of from about 0.1 to 10 parts by weight per part by weight of a diasonium salt.

The weight ratio of the 2-hydroxy-3-naphthoic acid amide derivative to the benzoylacetic amide derivative (I) preferably ranges from about 95:5 to 60:40. The optimum ratio can be easily determined by recording with variation of printing energy and selecting a ratio of the coupling components which causes the least deviation from a neutral gray color.

The above-described diazonium salt is preferably used in a total amount of from about 0.05 to 2.0 g/m$^2$.

The basic substances which can be used in the present invention are water-insoluble or sparingly water-soluble basic substances or substances capable of generating an alkali upon heating.

The basic substances that can be used include nitrogen-containing compounds, such as organic or inorganic ammonium salts, organic amines or amides, urea and thiourea or derivatives thereof, thiazoles, pyrroles, pyrimidines, piperazines, guanidines, indoles, imidazoles, imidazolines, triazoles, morpholines, piperidines, amidines, formamidines and pyridines. Specific examples of the nitrogen-containing compounds are ammonium acetate, tricyclohexylamine, tribenzylamine, octadecylbenzylamine, stearylamine, allylurea, thiourea, methylthiourea, allylthiourea, ethylenethiourea, 2-benzylimidazole, 4-phenylimidazole, 2-phenyl-4-methylimidazole, 2-undecylimidazoline, 2,4,5-trifuryl-2-imidazoline, 1,2-diphenyl-4,4-dimethyl-2-imidazoline, 2-phenyl-2-imidazoline, 1,2,3-triphenylguanidine, 1,2-ditolylguanidine, 1,2-dicyclohexylguanidine, 1,2,3-tricyclohexylguanidine, guanidine trichloroacetate, N,N'-dibenzylpiperazine, 4,4'-dithiomorpholine, morpholinium trichloroacetate, 2-aminobenzothiazole and 2-benzoylhydradinobenzothiazole. These basic compounds can be used alone or in combinations of two or more thereof. The basic substances having a pKa value of 7 to 14 are preferred.

The amount of the basic substance to be used is preferably from about 0.1 to 20 parts by weight per part by weight of the diazonium salt.

In the present invention, a core material containing the diazonium salt dissolved in a water-insoluble organic solvent is emulsified, and microcapsule walls are then formed around the emulsion droplets by polymerization. The organic solvents for dissolving the diazonium salt are preferably those having a boiling point of about 180° C. or higher, such as phosphoric esters, phthalic esters and other carboxylic acid esters, fatty acid amides, alkylated biphenyls, alkylated terphenyls, chlorinated paraffins, alkylated naphthalenes, diarylethanes, and the like. Specific examples of these organic solvents include tricresyl phosphate, trioctyl phosphate, octyldiphenyl phosphate, tricyclohexyl phosphate, dibutyl phthalate, dioctyl phthalate, dilauryl phthalate, dicyclohexyl phthalate, butyl oleate, diethylene glycol dibenzoate, dioctyl sebacate, dibutyl sebacate, dioctyl adipate, trioctyl trimellitate, acetyltriethyl citrate, octyl maleate, dibutyl maleate, isopropylbiphenyl, isoamylbiphenyl, chlorinated paraffins, diisopropylnaphthalene, 1,1'-ditolytethane, 2,4-di-t-aminophenol and N,N-dibutyl-2-butoxy-5-t-octylaniline. Of these, ester type solvents, e.g., dibutyl phthalate, tricresyl phosphate, diethyl phthalate, dibutyl maleate, etc., are particularly preferred.

The microcapsules of the present invention can be produced by emulsifying a core material containing a diazonium salt and forming walls of a high polymer around oil droplets of the core material. Reactants for forming the high polymer are added to the oil droplets or to the aqueous phase. Examples of the high polymer include polyurethane, polyurea, polyamide, polyester, polycarbonate, urea-formaldehyde resins, melamine resin, polystyrene, styrene-methacrylate copolymers, styrene-acrylate copolymers, gelatin, polyvinylpyrrolidone, polyvinyl alcohol, and the like. Preferred among them are polyurethane, polyurea, polyamide, polyester and polycarbonate, and more preferred are polyurethane and polyurea. These high polymers can be used alone or in a combination of two or more thereof.

It is preferable to add the reactants for polymerization to the inside of the oil droplets in view of obtaining microcapsules having a uniform size distribution in a short time and, thereby, providing recording materials excellent in working preservability. Details of this technique and compounds used therefor are disclosed in U.S. Pat. Nos. 3,726,804 and 3,796,669.

More specifically, in using polyurethane as a capsule material, a polyisocyanate and a second component which reacts with the polyisocyanate to form capsule walls, e.g., a polyol, are mixed in an oily liquid to be encapsulized, and the mixture is emulsified in water, followed by elevating the temperature to cause polymerization on the interface of the oil droplets. If necessary, a low boiling auxiliary solvent having a strong dissolving power can be added to the oily liquid.

Examples of suitable polyisocyanate and the polyol and polyamine reactive with the polyisocyanate are described in U.S. Pat. Nos. 3,281,383, 3,773,695 and 3,793,268, Japanese Patent Publication Nos. 40347/73 and 24159/74 and Japanese Patent Application (OPI) Nos. 80191/73 and 84086/73.

For the purpose of accelerating urethanation, tin salts and the like may be used in combination.

It is particularly preferred for obtaining satisfactory working preservability to use a polyisocyanate as a first wall forming material and a polyol as a second wall forming material. It is also possible to arbitrarily vary thermal permeability of capsule walls to reactants for color formation by appropriately selecting a combination of the polyisocyanate and the polyol to be used.

Specific examples of the polyisocyanate which can be used as a first wall forming material include diisocyanates, e.g., m-phenylene diisocyanate, p-phenylene diisocyanate, 2,6-tolylene diisocyanate, 2,4-tolylene diisocyanate, naphthalene-1,4-diisocyanate, diphenylmethane-4,4'-diisocyanate, 3,3'-dimethoxy-4,4'-biphenyldiisocyanate, 3,3'-dimethyldiphenylmethane-4,4'-diisocyanate, xylylene-1,4-diisocyanate, 4,4'-diphenylpropane diisocyanate, trimethylene diisocyanate, hexamethylene diisocyanate, propylene-1,2-diisocyanate, butylene-1,2-diisocyanate, cyclohexylene-1,2-diisocyanate and cyclohexylene-1,4-diisocyanate; triisocyanates, e.g., 4,4',4"-triphenylmethane triisocyanate and toluene-2,4,6-triisocyanate; tetraisocyanates, e.g., 4,4'-dimethyldiphenylmethane-2,2',5,5'-tetraisocyanate; and isocyanate prepolymers, e.g., an adduct of hexamethylene diisocyanate and trimethylolpropane, an adduct of 2,4-tolylene diisocyanate and trimethylolpropane, an adduct of xylylene diisocyanate and trimethylolpropane and an adduct of tolylene diisocyanate and hexanetriol.

The polyisocyanate is able to form a polymeric substance by the reaction with water.

Specific examples of the polyrols which can be used as a second wall forming material include aliphatic or aromatic polyhydric alcohols, hydroxy polyesters, hydroxy polyalkylene ethers, and the like.

In carrying out the encapsulation, watersoluble high polymers including anionic, nonionic and amphoteric high polymers can be used. Anionic high polymers, either natural or synthetic, include those having groups such as —COO⁻, —SO₃⁻, such as natural products, e.g., gum arabic and alginic acid; semisynthetic products, e.g., carboxymethyl cellulose, phthalylated gelatin, starch sulfate, cellulose sulfate and lignin sulfonic acid; and synthetic products, e.g., maleic anhydride (inclusive of hydrolysate thereof) type copolymers, (meth)acrylic acid type polymers and copolymers, vinylbenzenesulfonic acid type polymers and copolymers, and carboxyl-modified polyvinyl alcohol. Nonionic high polymers include polyvinyl alcohol, hydroxyethyl cellulose and methyl cellulose. The amphoteric high polymers include gelatin.

These water-soluble high polymers are used as an aqueous solution in concentration from about 0.01 to 10% by weight. The particle size of microcapsules is not greater than about 20 $\mu$m. In general, capsules exceeding about 20 $\mu$m are likely to deteriorate image quality. Where heat is applied with a thermal head to the side having a coated layer, particle sizes not greater than about 8 $\mu$m are preferred for avoiding pressure marks.

Microcapsules can be prepared from an emulsion containing at least about 0.2% by weight of components to be encapsulized such as a diazonium salt, an organic solvent, and the like.

The coupling components and the basic substance are present outside the microcapsules as solid particles dispersed to a particle size of not greater than about 10 $\mu$m, and preferably from about 0.2 to 7 $\mu$m, in a water-soluble high polymer solution by means of a sand mill, etc. The two coupling components may be dispersed either altogether or individually. Preferred water-soluble high polymers to be used as dispersing media are those used in the aforesaid encapsulization. The high polymer solution has a solids concentration of from about 2 to 30% by weight, and the coupling components and basic substance are added thereto in concentrations of from about 5 to 40% by weight, respectively.

The heat-sensitive recording materials in accordance with the present invention can contain pigments, e.g., silica, barium sulfate, titanium oxide, aluminum hydroxide, zinc oxide, calcium carbonate, etc., and fine powders, e.g., styrene beads, urea-melamine resin fine powders, etc., for the purpose of preventing sticking to a thermal head and improving writability.

The heat-sensitive recording materials of the present invention can also contain metal soaps for prevention of sticking. The amount of the metal soap to be added is from about 0.2 to 7 g/m².

The heat-sensitive recording material of the present invention can further contain a heat-melting material to increase a heat-recorded image density. The term "heat-melting material" as used herein means a substance that is solid at room temperature, has a melting point of from about 50° to 150° C., is capable of being melted by heating with a thermal head, and is capable of dissolving at least one of the diazonium salt, coupling components and basic substance. Such a heat-melting material includes fatty acid amides, N-substituted fatty acid amides, ketone compounds, N-substituted carbamate compounds, urea compounds, esters, and the like. These materials are used as a dispersion of particles having a size of from about 0.1 to 10 $\mu$m and in an amount of from about 0.2 to 7 g/m² solids content.

For the purpose of improving heat developability, the heat-sensitive recording materials of the present invention can furthermore contain hydroxyl compounds, carbamic ester compounds and aromatic methoxy compounds described in Japanese Patent Application No. 72382/84 (corresponding to U.S. Patent Application Ser. No. 721,978) and organic solfonamide compounds described in Japanese Patent Application No. 206832/84 (corresponding to U.S. Patent Application Ser. No. 721,978). These compounds are believed to decrease the melting point of the coupling components or basic substance or to improve heat permeability of microcapsule walls, thereby resulting in heightened practical image densities. They may be added to a core material to be encapsulized or may be present outside the microcapsules, with the former embodiment being preferred in view of the reduced amount required. In either embodiment, the amount of these compounds to be used in appropriately selected so as to obtain a desired color density, generally ranging from about 0.01 to 10 parts by weight, and preferably from about 0.1 to 5 parts by weight, per part by weight of the coupling components.

In addition, polymerizable vinyl monomers described in Japanese Patent Application No. 79831/84 (corresponding to U.S. Patent Application Ser. No. 725,197 now Pat. No. 4,737,484) may be incorporated in the core of the microcapsules in order to lessen yellowing of the background after photo-fixing. The vinyl monomer is added in an amount ranging from about 0.2 to 20 parts by weight, and preferably from abut 1 to 10 parts by weight, per part by weight of the diazonium salt.

In the present invention, it is possible to prevent fog by incorporating a coupling deactivator described in Japanese Patent Application No. 70509/84 (corresponding to U.S. patent application Ser. No. 721,521 now abandoned) to the aqueous phase of a coating composition. The coupling reaction deactivator outside the microcapsules reacts with any diazonium salt present in the aqueous phase or diazonium salt within incomplete capsules, i.e., diazonium salt which is not completely blocked by capsule walls, whereby the diazonium salt is inactivated to lose its coupling reactivity, i.e., color forming property.

The coupling reactivity deactivator is preferably colorless per se and of low side effect, and is more preferably water-soluble. The deactivator is used in an amount that does not hinder the color formation reaction of the diazonium salt within the microcapsules upon application of heat. Specifically, it is typically used in an amount of from about 0.01 to 2 moles, and preferably from about 0.02 to 1 mole, per mole of the diazonium salt.

In addition to the above-described components, the heat-sensitive recording materials of the present invention may contain an acid stabilizer, such as citric acid, tartaric acid, oxalic acid, boric acid, phosphoric acid, or pyrophosphoric acid.

The heat-sensitive recording materials of the present invention can be produced by coating a coating composition comprising the above-described components and an appropriate binder on a support, such as paper or a synthetic resin film.

The binder which can be used in the present invention includes various emulsions, such as polyvinyl alcohol, methyl cellulose, carboxymethyl cellulose, hydroxypropyl cellulose, gum arabic, gelatin, polyvinyl-pyrrolidone, casein, styrene-butadiene latexes, acrylonitrile-butadiene latexes, polyvinyl acetate, polyacrylic esters and ethylene-vinyl acetate copolymers. The amount to be used is from about 0.5 to 5 g/m² solids content.

Coating of the composition on a support can be carried out by any conventional coating method, such as bar coating, blade coating, air knife coating, gravure coating, roll coating, spray coating, dip coating, and the like. The coverage of the heat-sensitive layer is from about 2.5 to 25 g/m² dry solids content. The color forming substances may be individually coated in independent layers or be coated in one layer. A plurality of layers each containing all the color forming substances may be laminated. Further, a protective layer can be provided on the heat-sensitive layer.

As a support for the heat-sensitive recording materials of the present invention, neutral paper which is obtained by thermal extraction at pH 6 to 9 and sizing with a neutral sizing agent, e.g., alkyl ketene dimers, as described in Japanese Patent Application (OPI) No. 14281/80 (corresponding to U.S. Pat. No. 4,255,491) is advantageously employed from the standpoint of preservability with time.

Also, for preventing the permeation of the coating liquid into a paper support and improving the contact with the heat-sensitive recording layer with a thermal recording head, a paper having the ratio $$\frac{\text{stocking sizing degree}}{(\text{meter weighing capacity})^2} \geq 3 \times 10^{-3}$$

and a Beck smoothness of higher than 90 seconds, as described in Japanese Patent Application (OPI) No. 116687/82 (corresponding to U.S. Pat. No. 4,416,939) is advantageous.

Furthermore, a paper having the optical surface roughness of 8 microns or less and a thickness of from 40 to 75 microns described in Japanese Patent Application (OPI) No. 136492/83; a paper having a density of 0.9 c/m³ or less and an optical contact percentage of 15% or more as described in Japanese Patent Application (OPI) No. 69091/83; a paper manufactured from a pulp having a Canadian standard freeness (JIS P8121) of 400 cc or more for preventing the permeation of a coating liquid in the paper as described in Japanese Patent Application (OPI) No. 69097/83; a paper manufactured by Yankee paper machine the lustrous surface thereof is used as the coating surface for improving the coloring density and the resolving power as described in Japanese Patent Application (OPI) No. 65695/83 (corresponding to U.S. Pat. No. 4,466,007); and a paper subjected to a corona discharging treatment for improving the coating aptitude as described in Japanese Patent Application (OPI) No. 35985/84 can be used in this invention with good results.

Still further, various supports which are used in the field of ordinary heat-sensitive recording papers can be also used as the supports for the heat-sensitive recording materials of this invention.

The heat-sensitive recording materials according to the present invention can be applied to the field of facsimile or electronic calculators wherein high speed recording is demanded. They are also useful as a heat-developable copying paper. The heat-sensitive recording materials of the present invention are advantageous in that the unreacted diazonium salt after heat-recording can be fixed through decomposition by exposure to light.

The present invention will now be illustrated in greater detail with reference to the following examples, but it should be understood that the present invention is not limited thereto. In these examples, all parts and percents are given by weight unless otherwise indicated.

EXAMPLE 1

4 Parts of a diazonium salt having the following formula and 18 parts of a 3:1 adduct of xylylene diisocyanate and trimethylolpropane were dissolved in a mixed solvent of 24 parts of tricresyl phosphate and 5 parts of dichloromethane.

Diazonium Salt:

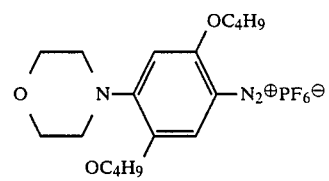

The resulting diazonium salt solution was added to a solution of 3.5 parts of polyvinyl alcohol, 1.7 parts of gelatin and 2.4 parts of 1,4-di(2-hydroxyethoxy)-benzene in 58 parts of water, and the mixture was emulsified at 20° C.

To the resulting emulsion was added 100 parts of water, and the mixture was heated at 60 ° C. for 2 hours while stirring to obtain a solution of microcapsules containing a diazo compound and having an average particle size of 3 μm.

18 Parts of 2-hydroxy-3-naphthoic acid anilide and 2 parts of 2,4-bis(benzoylacetamido)toluene were added to 100 parts of a 5% aqueous solution of polyvinyl alcohol and dispersed therein in a sand mill for about 24 hours to obtain a dispersion having an average particle size of 3 μm.

20 Parts of triphenylguanidine was added to 100 parts of a 5% aqueous solution of polyvinyl alcohol and dispersed therein in a sand mill for about 24 hours to obtain a dispersion having an average particle size of 3 μm.

Then, 20 parts of p-benzyloxyphenol was added to 100 parts of a 2.5% aqueous solution of polyvinyl alcohol and dispersed therein in a sand mill for about 24 hours to obtain a dispersion having an average particle size of 3 μm.

To 50 parts of the above obtained diazonium capsule solution were added 2 parts of a 5% potassium hydroquinonesulfonate solution, 15 parts of the above obtained coupling component dispersion, 15 parts of the triphenylguanidine dispersion and 20 parts of the p-benzyloxyphenol dispersion to prepare a coating composition.

The coating composition was coated on smooth fine paper having a basis weight of 50 g/m² to a dry weight of 10 g/m² by bar coating using a coating rod, followed by drying at 40° C. for 30 minutes to obtain a heat-sensitive recording material.

EXAMPLE 2

A heat-sensitive recording material was obtained in the same manner as described in Example 1 except for replacing the coupling components with 17 parts of 2-hydroxy-3-naphthoic acid anilide and 3 parts of benzoylacetic acid-4'-(4-toluenesulfonyloxy)-anilide.

EXAMPLE 3

A heat-sensitive recording material was obtained in the same manner as described in Example 1 except for replacing the coupling components with 17 parts of 2-hydroxy-3-naphthoic acid-4'-methylanilide and 3 parts of 1,2-bis(beozoylacetamido)benzene.

COMPARATIVE EXAMPLE 1

A heat-sensitive recording material was obtained in the same manner as described in Example 2 but using benzoylacetanilide instead of the benzoylacetic amide derivative.

COMPARATIVE EXAMPLE 2

A heat-sensitive recording material was obtained in the same manner as described in Example 2 but using 4-(4-1,1,3,3-tetramethylbutyl-phenyloxy)-acetoacetylanilide in place of the benzoylacetic amide derivative.

Test Method:

Heat-sensitive recording was conducted on each of the resulting heat-sensitive recording materials using a heat-sensitive printer, GIII mode ("UF-1000", manufactured by Matsushita Denso K. K.), with the heat energy applied being varied. The material was then exposed to light for fixing over the entire surface thereof by means of "Recopy Superdry 100" (manufactured by Rico Company Ltd.). The hue of the resulting image was as shown in Table 1 below.

On the other hand, the fixed areas were again subjected to a heat recording. As a result, it was found that the image recording was not carried out but it was fixed.

Working preservability of the materials was evaluated as follows. The heat-sensitive recording material was subjected to a forced deterioration test by preserving the unexposed material in the dark at 40° C. and 90% RH for 24 hours, and fog after the test as determined using a Macbeth densitometer was compared with the density of the background (fog) before the test. The results obtained are also shown in Table 1.

TABLE 1

| | | Fog | |
|---|---|---|---|
| Example No. | Hue of Image | Before Deterioration Test | After Deterioration Test |
| Example 1 | Black | 0.09 | 0.11 |
| Example 2 | Black | 0.09 | 0.11 |
| Example 3 | Black | 0.10 | 0.12 |
| Comparative Example 1 | Yellow-tinged at low density, blue-tinged at high density | 0.16 | 0.45 |
| Comparative Example 2 | Black | 0.15 | 0.29 |

As is apparent from Table 1 above, the heat-sensitive recording materials according to the present invention provide images of black hue with less fog and undergo only a small increase of fog after the forced deterioration test.

While the invention has been described in detail and with reference to specific embodiments thereof, it will be apparent to one skilled in the art that various changes and modifications can be made therein without departing from the spirit and scope thereof.

What is claimed is:

1. A heat-sensitive recording material comprising a support having provided thereon a heat-sensitive layer containing an admixture of (a) microcapsules containing at least one light-sensitive diazonium salt capable of azo-coupling with a 2-hydroxy-3-naphthoic acid anilide to develop a blue color, (b) a 2-hydroxy-3-naphthoic acid amide derivative, (c) a benzoylacetic amide derivative represented by the following formula (I) and (d) a basic substance, wherein said components (a), (b), (c) and (d) are contained in amounts sufficient to form a black color upon heat-developing, said black color being fixable by light:

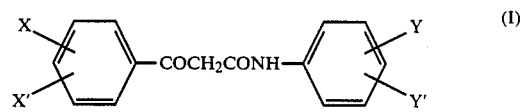

wherein X represents a hydrogen atom, a halogen atom, a lower alkyl group or an alkoxy, aralkyloxy, phenoxy or acylamino group having up to 18 carbon atoms; Y represents an alkyl or aralkyl group having from 7 to 18 carbon atoms, an alkoxy, aralkyloxy, phenoxy, naphthyloxy, alkylthio, aralkylthio or phenylthio group having from 6 to 18 carbon atoms, a naphthylthio group, a sulfonyloxy group, a sulfamoyl group, a ureido group, a thioureido group or an acylamino group; X' and Y' each represents a hydrogen atom, a halogen atom, a lower alkyl group or a lower alkoxy group; and Y and Y' may combine to form a substituted or unsubstituted benzene ring.

2. A heat-sensitive recording material as claimed in claim 1, wherein the 2-hydroxy-3-naphthoic acid amide derivative and the benzoylacetic amide derivative are present in a total amount of from about 0.1 to 10 parts by weight per part by weight of the diazonium salt.

3. A heat-sensitive recording material as claimed in claim 1, wherein the ratio of the 2-hydroxy-3-naphthoic acid amide derivative to the benzoylacetic amide derivative is from about 95:5 to 60:40 by weight.

4. A heat-sensitive recording material as claimed in claim 1, wherein the diazonium salt is present in a total amount of from about 0.05 to 2.0 g/m$^2$.

5. A heat-sensitive recording material as claimed in claim 1, wherein the basic substance is present in an amount of from about 0.1 to 20 parts by weight per part by weight of the diazonium salt.

6. A heat-sensitive recording material as claimed in claim 1, wherein the capsule wall of said microcapsules is a high polymer selected from polyurethane, polyurea, polyamide, polyester and polycarbonate.

7. A heat-sensitive recording material as claimed in claim 1, wherein said heat-sensitive layer further contains a hydroxyl compound, a carbamic ester compound, an aromatic methoxy compound and an organic sulfonamide compound.

8. A heat-sensitive recording material as claimed in claim 1, wherein the total carbon atoms of the X, Y, X' and Y' are 6 to 18.

* * * * *